United States Patent
Kittelsen et al.

(10) Patent No.: US 6,626,180 B1
(45) Date of Patent: Sep. 30, 2003

(54) QUADRUPLE COMPOSITE PERFORMANCE ENHANCING DENTAL APPLIANCE

(75) Inventors: Jon D. Kittelsen, Fridley, MN (US); Henry D. Cross, III, Murrell's Inlet, SC (US); Paul C. Belvedere, Edina, MN (US); Mark Herman, Minneapolis, MN (US)

(73) Assignee: Bite Tech, Inc., Minneapolis, MN (US)

( * ) Notice: Subject to any disclaimer, the term of this patent is extended or adjusted under 35 U.S.C. 154(b) by 162 days.

(21) Appl. No.: 09/657,421

(22) Filed: Sep. 8, 2000

(51) Int. Cl.[7] .................................................. A61C 5/14
(52) U.S. Cl. ........................ 128/859; 128/861; 128/862
(58) Field of Search ................................ 128/846, 848, 128/859–862; 602/902; 433/6

(56) References Cited

U.S. PATENT DOCUMENTS

| 257,038 A | 4/1882 | McMann |
|---|---|---|
| 1,117,928 A | 11/1914 | Thurmond |
| 1,323,832 A | 12/1919 | Chige |
| 1,461,209 A | 7/1923 | Josiah |
| 1,470,888 A | 10/1923 | Smedley |
| 1,487,392 A | 3/1924 | Lee |
| 2,118,980 A | 5/1938 | Montgomery |
| 2,257,709 A | 9/1941 | Anderson |
| 2,423,005 A | 6/1947 | Chaiken |
| 2,630,117 A | 3/1953 | Coleman |
| 2,643,652 A | 6/1953 | Cathcart |
| 2,659,366 A | 11/1953 | Savarese |
| 2,669,988 A | 2/1954 | Carpenter |
| 2,678,043 A | 5/1954 | Stark |
| 2,694,397 A | 11/1954 | Herman |
| 2,702,032 A | 2/1955 | Freedland |
| 2,708,931 A | 5/1955 | Freedland |
| 2,750,941 A | 6/1956 | Cathcart |
| 2,833,278 A | 5/1958 | Ross |
| 2,847,003 A | 8/1958 | Helmer |
| 2,933,811 A | 4/1960 | Lifton |
| 2,966,908 A | 1/1961 | Cathcart |
| 3,016,052 A | 1/1962 | Zubren |
| 3,058,462 A | 10/1962 | Greenblum |
| 3,073,300 A | 1/1963 | Berghash |
| 3,082,765 A | 3/1963 | Helmer |
| 3,107,667 A | 10/1963 | Moore |

(List continued on next page.)

FOREIGN PATENT DOCUMENTS

| CA | 1147583 | 8/1983 |
| DE | 480423 | 8/1929 |

OTHER PUBLICATIONS

Mouth Protectors: Give Your Teeth a Sporting Chance; American Dental Association, 1985.
Muscular Strength Correlated to Jaw Posture and the Temporomandibular Joint; NYS Dental Journal, vol. 44, No. 7, Aug.–Sep., 1978.
Reductions of Stress in the Chewing Mechanism—Part III, W. B. May, D.D.S..

Primary Examiner—Michael A. Brown
(74) Attorney, Agent, or Firm—Gerald E. Helget; Nelson R. Capes; Briggs and Morgan

(57) ABSTRACT

A performance enhancing and force absorbing dental appliance adapted to lie within the mouth of an athlete consists of an occlusal posterior pad made of quadruple composite material comprising four layers of distinct materials, further comprising a first layer of a durable, resilient material; a second layer of non-softenable, flexible material; a third layer of a hard, very durable material; and a fourth layer of a softenable material, engageable with the occlusal surfaces to space apart the upper and lower teeth, to absorb shock and clenching stress. An adjustable arch adapted to expand and contract to be molded to the palate is provided connecting the posterior pads together within the mouth and out of the way of the tongue to maintain the position of the occlusal posterior pads within the mouth during use and to prevent loss of the pads such as by swallowing. An expandable serpentine bridge may be embedded in the arch.

36 Claims, 6 Drawing Sheets

U.S. PATENT DOCUMENTS

| | | | |
|---|---|---|---|
| 3,124,129 | A | 3/1964 | Grossberg |
| 3,126,002 | A | 3/1964 | Owens |
| 3,203,417 | A | 8/1965 | Helmer |
| 3,207,153 | A | 9/1965 | Goldstein |
| 3,223,085 | A | 12/1965 | Gores et al. |
| 3,247,844 | A | 4/1966 | Berghash |
| 3,312,218 | A | 4/1967 | Jacobs |
| 3,319,626 | A | 5/1967 | Lindsay |
| 3,407,809 | A | 10/1968 | Ross |
| 3,411,501 | A | 11/1968 | Greenberg |
| 3,416,527 | A | 12/1968 | Hoef |
| 3,448,738 | A | 6/1969 | Berghash |
| 3,457,916 | A | 7/1969 | Wolicki |
| 3,485,242 | A | 12/1969 | Greenberg |
| 3,496,936 | A | 2/1970 | Gores |
| 3,505,995 | A | 4/1970 | Greenberg |
| 3,513,838 | A | 5/1970 | Foderick et al. |
| 3,518,988 | A | 7/1970 | Gores |
| 3,532,091 | A | 10/1970 | Lerman |
| 3,682,164 | A | 8/1972 | Miller |
| 3,692,025 | A | 9/1972 | Greenberg |
| 3,768,465 | A | 10/1973 | Helmer |
| 3,864,832 | A | 2/1975 | Carlson |
| 3,916,527 | A | 11/1975 | Linkow |
| 3,924,638 | A | 12/1975 | Mann |
| 3,943,924 | A | 3/1976 | Kallestad et al. |
| 4,030,493 | A | 6/1977 | Walters et al. |
| 4,044,762 | A | 8/1977 | Jacobs |
| 4,063,552 | A | 12/1977 | Going et al. |
| 4,114,614 | A | 9/1978 | Kesling |
| 4,185,817 | A | 1/1980 | Peterson |
| 4,211,008 | A | 7/1980 | Lerman |
| 4,330,272 | A | 5/1982 | Bergersen |
| 4,337,765 | A | 7/1982 | Zimmerman |
| 4,348,178 | A | 9/1982 | Kurz |
| 4,376,628 | A | 3/1983 | Aardse |
| 4,457,708 | A | 7/1984 | Dufour |
| 4,490,112 | A | 12/1984 | Tanaka et al. |
| 4,495,945 | A | 1/1985 | Liegner |
| 4,519,386 | A | 5/1985 | Sullivan |
| 4,568,280 | A | 2/1986 | Ahlin |
| 4,591,341 | A | 5/1986 | Andrews |
| 4,640,273 | A | 2/1987 | Greene et al. |
| 4,671,766 | A | 6/1987 | Norton |
| 4,672,959 | A | 6/1987 | May et al. |
| 4,727,867 | A | 3/1988 | Knoderer |
| 4,755,139 | A | 7/1988 | Abbatte et al. |
| 4,763,791 | A | 8/1988 | Halverson et al. |
| 4,765,324 | A | 8/1988 | Lake, Jr. |
| 4,791,941 | A | 12/1988 | Schaefer |
| 4,793,803 | A | 12/1988 | Martz |
| 4,799,500 | A | 1/1989 | Newbury |
| 4,810,192 | A | 3/1989 | Williams |
| 4,838,283 | A | 6/1989 | Lee, Jr. |
| 4,848,365 | A | 7/1989 | Guarlotti et al. |
| 4,867,147 | A | 9/1989 | Davis |
| 4,944,947 | A | 7/1990 | Newman |
| 4,955,393 | A | 9/1990 | Adell |
| 4,976,618 | A | 12/1990 | Anderson |
| 4,977,905 | A | 12/1990 | Kittelsen et al. |
| 4,989,616 | A | 2/1991 | Lee, Jr. |
| 5,031,611 | A | 7/1991 | Moles |
| 5,031,638 | A | 7/1991 | Castaldi |
| 5,063,940 | A | 11/1991 | Adell et al. |
| 5,076,785 | A | 12/1991 | Tsai |
| 5,082,007 | A | 1/1992 | Adell |
| 5,103,838 | A | 4/1992 | Yousif |
| 5,112,225 | A | 5/1992 | Diesso |
| 5,117,816 | A | 6/1992 | Shapiro et al. |
| D328,494 | S | 8/1992 | Schwendeman et al. |
| 5,152,301 | A | 10/1992 | Kittelsen et al. |
| 5,154,609 | A | 10/1992 | George |
| 5,165,424 | A | 11/1992 | Silverman |
| 5,174,284 | A | 12/1992 | Jackson |
| 5,194,003 | A | 3/1993 | Garay et al. |
| 5,194,004 | A | 3/1993 | Bergersen |
| 5,203,351 | A | 4/1993 | Adell |
| 5,234,005 | A | 8/1993 | Kittelsen et al. |
| 5,235,991 | A | 8/1993 | Minneman |
| 5,259,762 | A | 11/1993 | Farrell |
| 5,277,203 | A | 1/1994 | Hays |
| D343,928 | S | 2/1994 | Kittelsen |
| 5,293,880 | A | 3/1994 | Levitt |
| 5,297,960 | A | 3/1994 | Burns |
| 5,299,936 | A | 4/1994 | Ueno |
| 5,302,117 | A | 4/1994 | Kraut et al. |
| 5,313,960 | A | 5/1994 | Tomasi |
| 5,316,474 | A | 5/1994 | Robertson |
| 5,320,114 | A | 6/1994 | Kittelsen et al. |
| 5,323,787 | A | 6/1994 | Pratt |
| 5,328,362 | A | 7/1994 | Watson et al. |
| 5,336,086 | A | 8/1994 | Simmen et al. |
| 5,339,832 | A | 8/1994 | Kittelsen et al. |
| 5,353,810 | A | 10/1994 | Kittelsen et al. |
| 5,365,946 | A | 11/1994 | McMillan |
| 5,385,155 | A | 1/1995 | Kittelsen et al. |
| 5,386,821 | A | 2/1995 | Poterack |
| D356,188 | S | 3/1995 | Kittelsen |
| 5,401,234 | A | 3/1995 | Libin |
| 5,406,963 | A | 4/1995 | Adell |
| 5,447,168 | A | 9/1995 | Bancroft |
| 5,460,527 | A | 10/1995 | Kittelsen |
| 5,469,865 | A | 11/1995 | Minneman |
| 5,490,520 | A | 2/1996 | Schaefer et al. |
| 5,511,562 | A | 4/1996 | Hancock |
| 5,513,656 | A | 5/1996 | Boyd, Sr. |
| 5,533,524 | A | 7/1996 | Minneman |
| D373,421 | S | 9/1996 | Brown |
| 5,566,684 | A | 10/1996 | Wagner |
| 5,584,687 | A | 12/1996 | Sullivan et al. |
| 5,586,562 | A | 12/1996 | Matz |
| 5,590,643 | A | 1/1997 | Flam |
| 5,592,951 | A | 1/1997 | Castagnaro et al. |
| 5,624,257 | A | 4/1997 | Farrell |
| 5,636,379 | A | 6/1997 | Williams |
| 5,646,216 | A | 7/1997 | Watson et al. |
| 5,649,534 | A | 7/1997 | Briggs, III |
| 5,666,973 | A | 9/1997 | Walter |
| 5,692,523 | A | 12/1997 | Croll et al. |
| 5,718,243 | A | 2/1998 | Weatherford et al. |
| 5,718,575 | A | 2/1998 | Cross, III |
| 5,730,599 | A | 3/1998 | Pak |
| 5,746,221 | A | 5/1998 | Jones et al. |
| D397,442 | S | 8/1998 | Kittelsen |
| 5,816,255 | A | 10/1998 | Fishman et al. |
| 5,819,744 | A | 10/1998 | Stoyka, Jr. |
| 5,823,193 | A | 10/1998 | Singer et al. |
| 5,823,194 | A | 10/1998 | Lampert |
| 5,826,581 | A | 10/1998 | Yoshida |
| 5,836,761 | A | 11/1998 | Belvedere et al. |
| 5,865,619 | A | 2/1999 | Cross, III et al. |
| 5,873,365 | A | 2/1999 | Brown |
| 5,879,155 | A | 3/1999 | Kittelsen |

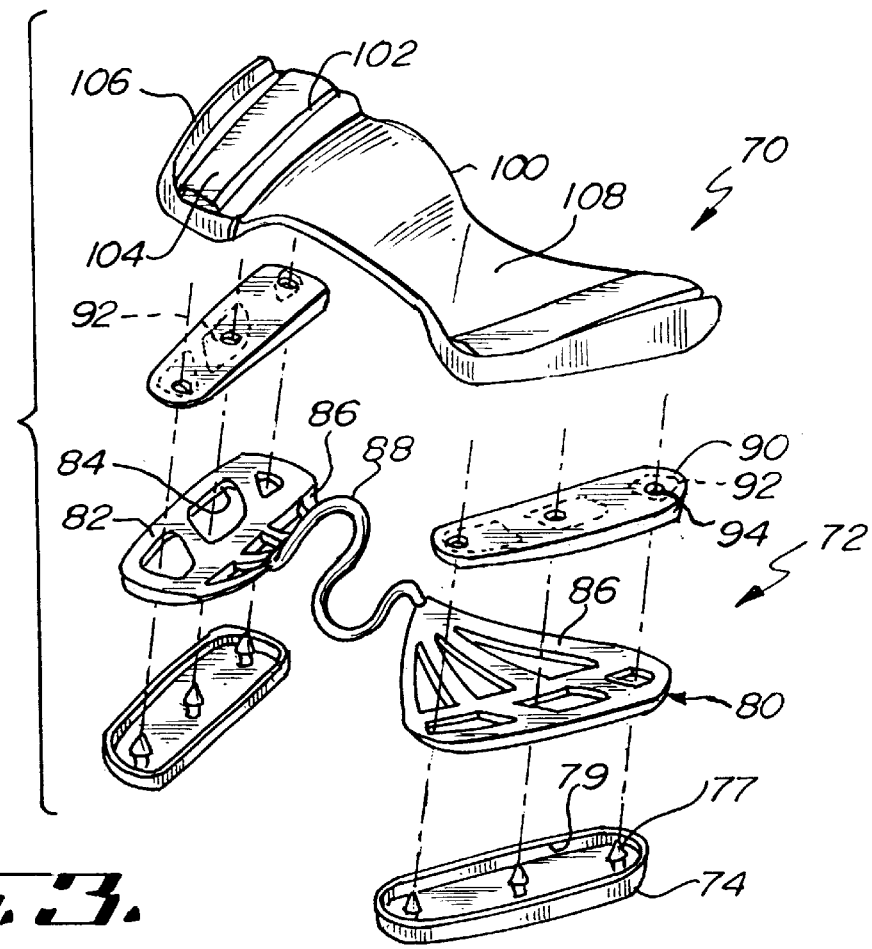
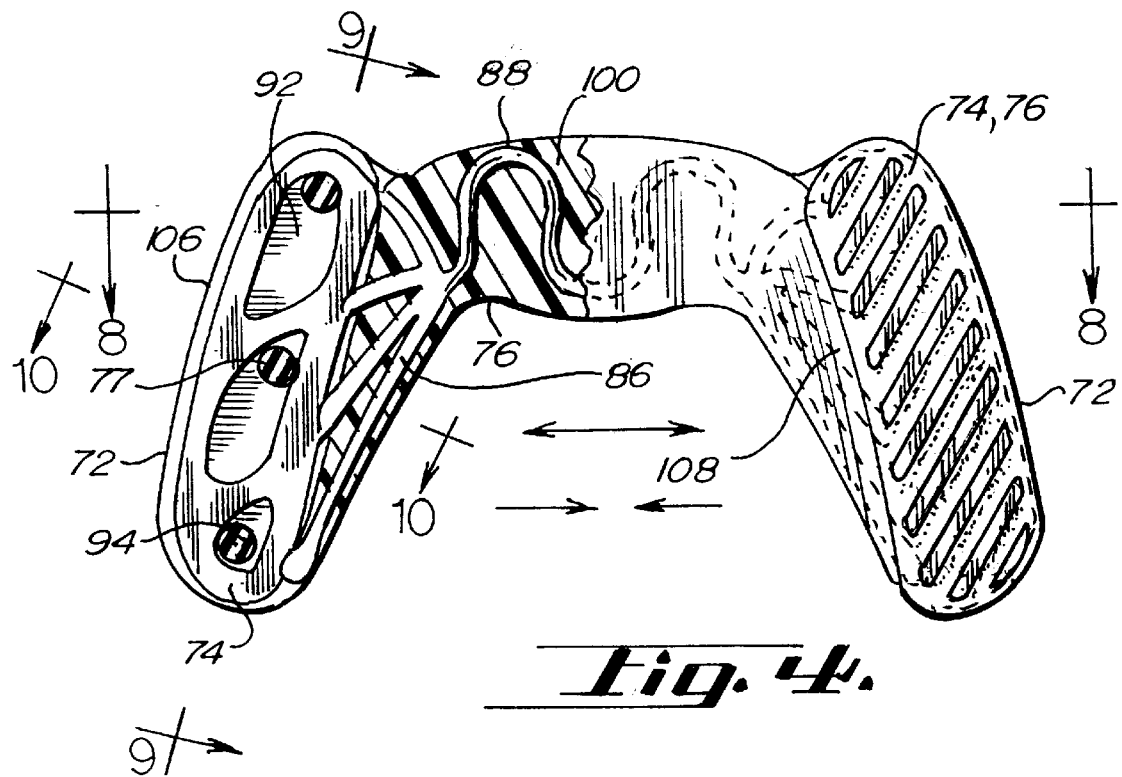

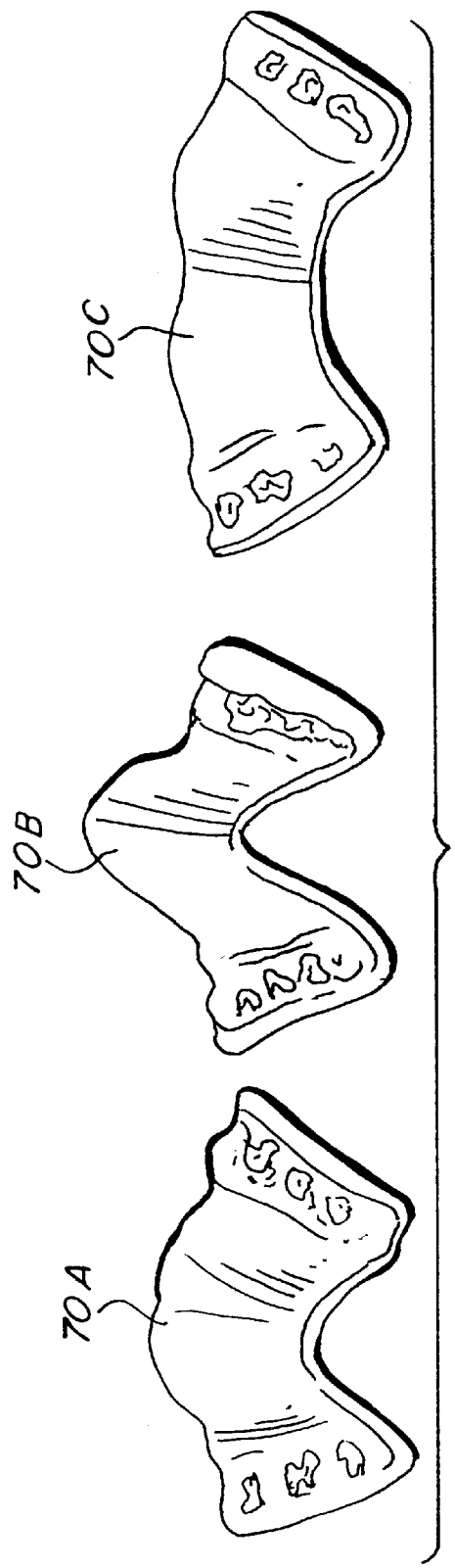
Fig. 12. Fig. 13. Fig. 14.

QUADRUPLE COMPOSITE PERFORMANCE ENHANCING DENTAL APPLIANCE

BACKGROUND OF THE INVENTION

This invention relates generally to a performance enhancing and force absorbing quadruple composite dental appliance for use by athletes, and more particularly to such an adjustable, customizable appliance that spaces apart the teeth to absorb shock and clenching stress, to space apart the anterior teeth of the lower and upper jaws to facilitate breathing and speech, to lessen condyle pressure, force and impact upon the cartilage and temporomandibular joints, the arteries and the nerves, and to further increase body muscular strength and endurance.

Almost all athletes, such as body builders, weight lifters, baseball batters, golfers, football players, hockey players and bowlers, clench their teeth during exertion which results in hundreds of pounds of compressed force exerted from the lower jaw onto the upper jaw.

This clenching force is unevenly transmitted through the jaw structure into the connective tissues and muscles of the lower jaw and further into the neck and back. This can result in headaches, muscle spasms, damage to teeth, injury to the temporomandibular joint, and pain in the jaw. Furthermore, clenching the teeth makes breathing more difficult during physical exercise and endurance when breathing is most important.

The natural inclination to clench the jaw during physical exertion is impossible to avoid. One theory is that this is an ancient reflex designed to protect the caveman's jaw from displacement or fracture. An injury to ancient man's jaw meant almost certain death from starvation. Man still instinctively clenches his teeth to lock his jaw into a safe position during aggression or physical activity to protect his jaw. But when the teeth are clenched, the body puts an upper limit on one's strength so that one can't overclench and damage one's teeth and jaw structures.

There are over 60 million overweight Americans today. Spending in the diet aid category equals $1.06 billion annually. Research shows that use of a dental appliance to prevent damage to the teeth during clenching helps to increase the productivity of an aerobic workout by increasing endurance and muscle activity and therefore calorie burn.

More than 80% of the population has some measure of improper jaw alignment, causing painful chewing, tooth grinding, migraine headaches, stress or several of these problems at once. The temporomandibular (TM) artery runs directly through the TM joint. This main artery carries oxygenated blood to the arteries in the face and head. When the TM joint is properly balanced, blood flows freely to these areas, which is believed to lessen the incidence of headache and stress. When the TM joint is out of balance or improperly aligned, undue stress is placed on this vital artery and the corresponding muscle groups.

Each year, reports the Journal of the American Dental Association, dentists make approximately 3.6 million anti-bruxing devices for their tooth grinding patients. Sizing and fitting in the past has required dental assistance. At an average cost of $275 (but sometimes much higher), this equates to a one billion dollar market. Nocturnal tooth grinding is a major pain—powerful enough to crack a walnut at 250 pounds per square inch, the pressure is ten times the force registered during normal chewing. Bruxing causes the teeth to wear down at odd angles, affecting the shape of the face, causing migraine headaches and muscle soreness and aggravating TMJ disorders.

The market for over-the-counter analgesics in the U.S. was $2.91 billion in 1996. An estimated 18 million people suffer from migraine headaches, another 6 million form back and neck pain. While almost 3 million Americans are treated annually by pain clinics, many more remain in need due to inadequate insurance or denial of benefits for such treatment. Studies have shown that increasing the blood flow to the arteries of the face can help reduce headache pain. Repositioning the jaw by a dental appliance to alleviate stress and pain acts as a drug-free remedy to millions of stress and headache sufferers by temporarily restoring blood flow to the face and head.

It is well known that the birthing process creates a tremendous amount of physiological and psychological stress upon the mother. In fact, pregnant women go through weeks, if not months, of physical exercise to prepare them for the exertions necessary during the birth of their child. The actual birthing process is very analogous to athletes as women about to give birth may very well clench their teeth during the exertion of labor.

Rehabilitation relative to heart attacks, operations and injuries also require exertion and can be facilitated by an increased blood flow to the brain and return back to good conditioning with exercise.

Snoring occurs when the mouth is open and the tongue moves back into the throat. This causes the airway passage to narrow which increases the likelihood of snoring. It is known that moving the condyle of the lower jaw forward in a way will increase the airway and assist in the elimination of snoring.

It is believed that consciousness and the ability to focus is increased with an object in the mouth. This causes one to salivate, focus and be more awakened with improved concentration, hand eye coordination, and even thought process which otherwise would be non-voluntary reactions.

U.S. Pat. No. 5,584,687 discloses a singular material performance enhancing dental appliance. U.S. Pat. Nos. 5,865,619 (the '619 patent) and U.S. Pat. No. 6,012,919 (the '919 patent) disclose a triple composite performance enhancing dental appliance. Applicant has found that the embodiments of the '687 patent, the '619 patent and the '919 patent have several deficiencies that Applicant has corrected in the instant invention.

Most importantly, many problems exist with prior dental appliances having posterior pads and a connective arch. Labial or buccal walls did not accept wide teeth, were bulky and had sharp edges. Arches medially located across the palate caused gagging and speech impediments, as well as fitting problems. Weak arches cause the appliances to collapse and permit the pads to touch and stick together upon removal from hot water. Thus, fitting of such appliances has always been a problem. Wide posterior teeth and deep and shallow palates required multiple sizes which were difficult for the consumer to choose from, let alone fit. Delamination and chewing destruction caused short life.

The present invention solves the prior art problems and discloses an appliance suitable for all the above needs and uses, plus many more, which will be appreciated with a review of the specification, claims and figures.

SUMMARY OF THE INVENTION

A performance enhancing and force absorbing dental appliance adapted to lie within the mouth of an athlete consists of occlusal posterior pads made of quadruple composite material comprising four layers of distinct materials and a connective arch. The first bottom layer traction pad is of a durable, resilient elastomeric gripping material. The second layer is of non-softenable, flexible, shape maintaining framework material that is expandable and contractible. The third layer is of a hard, very durable wedge-shaped bite plate material. The fourth arch layer is of a softenable material, moldable to fit and grip the posterior teeth and anterior palate. The fourth material substantially encloses the appliance. The four materials are physically interlocked. An anti-microbial agent may be added to the materials.

A principal object and advantage of the present invention is that the appliance protects the teeth, jaws, gums, connective tissues, back, head and muscles from teeth clenching forces typically exerted during athletic activity and birthing.

Another object and advantage of the present invention is that it facilitates breathing and speech during strenuous physical activity such as in power lifting or bodybuilding.

Another object and advantage of the present invention is that the appliance places the lower jaw in the power position moving the condyle downwardly and forwardly away from the nerves and arteries within the fossae or socket to raise body muscular strength, greater endurance and improved performance by the appliance user.

Another object and advantage of the present invention is that the appliance is customizable to fit the width and configurations of the upper posterior teeth and the palate structure of any user. Teeth width, spacing from one side of the mouth to the other side of the mouth and palate height varies substantially from person to person.

Another object and advantage of the present invention is that it allows the wearer to increase effort and calorie burn during a workout by preventing the clenching reflex from limiting bodily strength and endurance.

Another object and advantage of the present invention is that it prevents grinding of the teeth (bruxing).

Another object and advantage of the present invention is that helps to alleviate pain such as migraine headache by properly positioning the lower jaw and increasing the blood flow through the temporomandibular artery and associated circulatory and nerve systems.

Another object and advantage of the present invention is that allows a woman to increase the force with which she bears down during labor contractions, without harming the teeth and associated oral structures.

Another object and advantage of the present invention is that it assists in the rehabilitation process of recovering from injury or heart attacks by increasing the flow of blood and oxygen to the brain.

Another object and advantage of the present invention is that it increases consciousness and is believed to have a systemic action that can alter non-voluntary reactions to external stimuli to make the appliance wearer more conscientious, focused, awake and ready.

Another object and advantage is that the present invention reduces snoring by moving the condyle forward and further opening up the airway passage.

Another object and advantage of the present invention is that it has a tough, rubbery, elastomeric, unpenetrable bottom layer or traction pad engaging and gripping the lower teeth which prevents the appliance from being chewed through and assures long life to the appliance.

Another object and advantage of the present invention is that it has a second layer of a non-softenable, flexible material. This material is extended in a serpentine bridge and cross-cantilever connectors that supports the appliance after heating to maintain shape and guides the upper teeth during the fitting process.

Another object and advantage of the present invention is that it has a third layer of a hard, very durable material that acts as a bite plate, reverse wedge or fulcrum that cannot be penetrated by the teeth, giving the appliance a longer life cycle.

Another object and advantage of the present invention is that the occlusal pads and the adjustable arch are preferably made of a fourth layer of a softenable material which will permit the user to refit the appliance should the appliance not originally fit properly.

Another object and advantage of the present invention is that the fourth layer has been extended over the second and third layers and provides for the formation of a smooth, labial wall, greatly increasing comfort and avoiding sharp edges. This allows the user to manipulate the softenable material and custom fabricate a labial wall that will accormnodate any tooth width and palate depth or height.

Another object and advantage of the present invention is that eliminating a rigid labial wall also decreases the amount of material between the teeth and cheek, making the appliance more comfortable and less intrusive and cumbersome. Less material also makes the appliance less visible and bulky in the wearer's mouth. Furthermore, the absence of a rigid labial wall results in less pressure and squeezing on the teeth, improving comfort and fit.

Another object and advantage is that the arch is dramatically canted forwardly toward the anterior teeth of the upper jaw, greatly increasing comfort and reducing gagging and speech impediment.

Another object and advantage of the present invention is that an anti-microbial and/or anti-bacterial ingredient keeps the appliance free of germs or odor causing microbials and bacteria during non-use and storage.

Another object and advantage of the present invention is that the mechanically interlocked four materials will not separate with use or chewing by the user which is common with athletes. This secure interlock of the materials is further supported by heat, pressure and ultimate compatible chemical bonding.

Another object and advantage is that the wearer of the appliance experiences decreased heart rate and quicker recovery during aerobic exercise and activity.

Another object and advantage is that wearing the present invention increases dopamine concentration for increased motor activity.

Another object and advantage is that the appliance is ideal for health and wellness, birthing, industrial, dental, bruxing, exercise, awareness and athletic competition and protection.

Another object and advantage is that the Belvedere bridge, Cross cantilever connectors and occlusal pad plates of the non-softening but flexible framework maintains appliance shape during heating and fitting and permits expansion and contraction to fit any teeth and palate.

Other objects and advantages will become obvious with the reading of the following specification and appended claims with a review of the figures.

BRIEF DESCRIPTION OF THE DRAWINGS

FIG. 3 is an exploded perspective view of the dental appliance of the present invention;

FIG. 4 is a bottom plan view partially broken away of the dental appliance of the present invention;

FIG. 12 is a bottom plan view partially broken away showing another traction pad configuration;

FIG. 13 is a view similar to FIG. 12 showing another traction pad configuration; and FIG. 14 is a perspective view collectively showing three different form-fitted appliances for different people made from the same invention.

DETAILED DESCRIPTION OF THE PREFERRED EMBODIMENT

Figure 1:
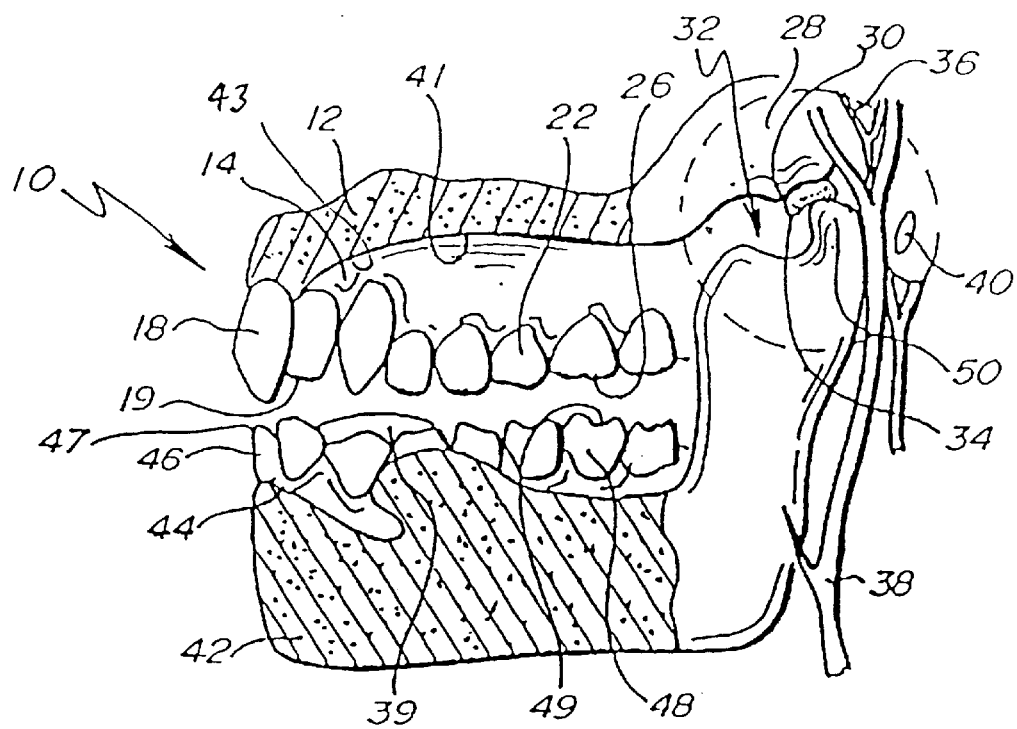
FIG. 1 is a maxillary mandibular buccal or partial side elevational view of the jaws and temporomandibular joint of the user of the dental appliance of the present invention.
Figure 1A:
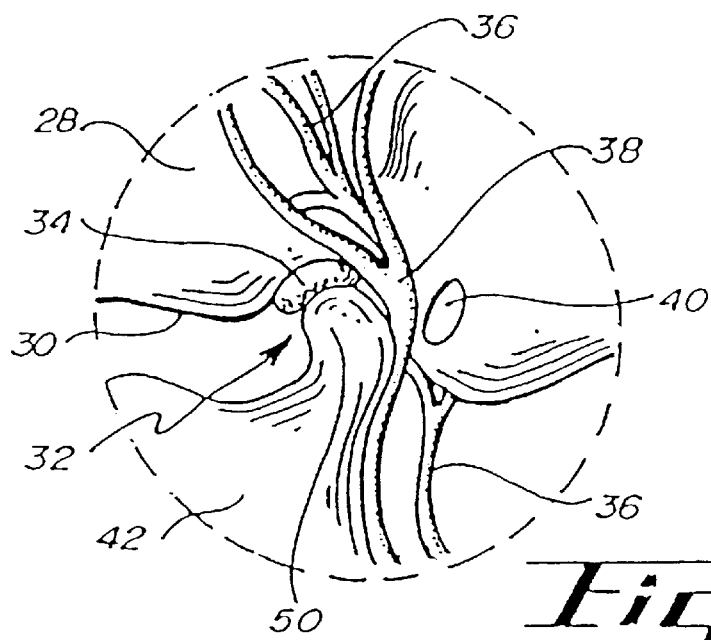
FIG. 1A is an enlarged view of the temporomandibular joint portion of FIG. 1.

To understand the structural features and benefits of the dental appliance 70 of the present invention, some anatomy will first be described. Referring to FIGS. 1 and 1A, the user or athlete has a mouth 10 generally comprised of a rigid upper jaw 12 and a moveable lower jaw 42 which are movably connected at the temporomandibular joint (TMJ) 32 and 50.

More specifically, the rigid upper jaw 12 has gum tissue 14 within mouth 10. Gum tissue 14, as well as the bone thereunder, supports anterior teeth (incisors and canines) 18 which have incisal or biting surfaces 19. The gum tissues 14 and the bone thereunder also support posterior teeth (molars and bicuspids) 22 which have cusps or biting surfaces 26.

Referring to one side of the human head, the temporal bone 28 is located upwardly and rearwardly of the upper jaw 12 and is in the range of 1/16 to 1/32 inch thick. The articular eminence 30 forms the beginning of the fossae 32 or the socket of the temporomandibular joint 32 and 50.

Rearwardly and posteriorly to the articular eminence 30 is located cartilage 34. Through the temporomandibular joint 32 and 50 pass the auriculo-temporalis nerve 36 and the supra-temporo artery 38. Posteriorly to this structure is located the inner ear 40. Within the mouth is located tongue 39 and the roof or hard palate 41, which terminates rearwardly into the soft palate and forwardly into the anterior palate or ruggae 43. The ruggae 43 has a ribbed surface which is identifiable by fingers or tongue 39.

The movable jaw or mandible 42 supports a bone covered by gum tissue 44 which further supports anterior teeth (incisors and canines) 46 with incisal or biting surfaces 47 and posterior teeth (molars and bicuspids) 48 with occlusal biting surfaces 49. The condyle 50 of the lower jaw 42 forms the ball of the temporomandibular joint 32 and 50. The anatomical structure is the same for both sides of the head.

Repeated impacts, collisions, blows, stress or forces exerted on the movable lower jaw 42 result in excessive wearing forces upon the condyle 50 and the cartilage, meniscus, or disc 34—typically resulting in bone deterioration on the head of the condyle or slippage and compressive damage of the cartilage 34. Thereafter, the lower jaw 42 may be subject to irregular movement, pain, loss of comfortable range of movement and clicking of the joint 32 and 50.

The auriculo-temporalis nerve 36 relates to both sensory and motor activity of the body. Any impingement or pinching of this nerve 36 can result in health problems as previously mentioned. The supra-temporal artery 38 is important in that it provides blood circulation to portions of the head. Impingement, pinching, rupture or blockage of this artery 38 will result in possible loss of consciousness and reduced physical ability and endurance due to the restriction of blood flow to portions of the brain. Thus, it is extremely important to assure that the condyle 50 does not impinge upon the auriculo-temporalis nerve 36 or the supra-temporal artery 38.

It is also important to note that the temporal bone 28 is not too thick in the area of the glenoid fossae. Medical science has known that a sharp shock, stress, or concussive force applied to the lower jaw 42 possibly could result in the condyle 50 protruding through the glenoid fossae of the temporal bone 28, thereby causing death. There is a suture line (growth and development seam) in the glenoid fossae, resulting in a possible weakness in the fossae in many humans. This incident rarely, but sometimes, occurs with respect to boxing athletes.

The dental appliance of the present invention is shown in the Figures as reference numeral 70.

The dental appliance 70 has a pair of quadruple-composite occlusal pads 72, comprised of four layers of distinct materials 74, 80, 90 and 100. Each pad may or may not have a preformed moldable labial or buccal wall 82 (present in FIGS. 3, 8 and 10). The absence of a rigid labial wall assures comfortable fitting for any width of mouth and posterior teeth 22.

The materials may have antimicrobial or antibacterial agents added. Swiss made Triclosan® by Siba Giegy or Microban® by Microban of Huntersville, N.C. 20808 are acceptable agents.

The traction pads or first layer 74 contacts and grips the occlusal biting surfaces 49 of the posterior teeth 48 of the lower jaw and is composed of a durable, resilient material which deforms somewhat when the jaws are closed and cushions the teeth 48 of the lower jaw.

The durable, resilient material of the first layer 74 comprises a mixture of a styrene block copolymer and ethylene vinyl acetate (EVA). A suitable styrene block copolymer is available as DYNAFLEX® part number G2782 from GLS Corporation, Thermoplastic Elastomers Division, 833 Ridgeview Dr., McHenry, Ill. 60050. EVA is available from a number of sources, such as the ELVAX® resins from Dupont Packaging and Industrial Polymers, 1007 Market Street, Wilmington, Del. 19898. It is desirable that the durable, resilient material have a Shore "A" hardness of 82, which is very durable, yet rubbery.

In a second embodiment, the durable, resilient material of the first layer 74 comprises a mixture of a styrene block copolymer as described above and a polyolefin elastomer. Preferably, the polyolefin elastomer is a copolymer of ethylene and octene-1. A suitable copolymer is available as ENGAGE® from Dupont Canada, Inc., P.O. Box 2200, Streetsville, Mississauga, Ontario L5M 2H3.

In a third embodiment, the durable, resilient material of the first layer 74 comprises a mixture of a thermoplastic rubber and a polyolefin elastomer as described above. Suitable thermoplastic rubbers are Santoprene® from Advanced Elastomer Systems, L.P., 388 South Main Street, Akron, Ohio 44311 and Kraton® thermoplastic rubber from the Shell Oil Company, Houston, Tex. Kraton® is composed of a styrene-ethylene/butylenes-styrene block copolymer and other ingredients. The composition of Santoprene® is a trade secret.

The second layer 80 is composed of a non-softenable, flexible material that rigidly holds its shape in hot water and will not melt during molding of succeeding materials 90 and 100. Polypropylene (co-polymer) is suitable. Polypropylene part number AP6112-HS from Huntsman Corporation, Chesapeake, Va. 23320, has a melting point of 386° F. The second layer includes a connected framework 80 including the pad plate 82, cross-cantilevered connectors 86 and the serpentine Belvedere bridge 88.

High-density polyethylene is a typical material. A suitable high-density polyethylene is HD-6706 ESCORENE® Injection Molding Resin from ExxonMobil Chemical Company, P.O. Box 3272, Houston, Tex. 77253-3272. This material is a linear polyethylene or ethylene-olefin copolymer. The third layer must be hard enough so that it cannot be penetrated by the teeth under maximum biting pressure and thereby forms a bite plate 90.

The fourth arch layer 100 comprises a softenable material contacting the teeth of the upper jaw and encapsulating the framework 80, bite plate 90 and partially the traction pads 74. Typically, the material is softenable by heat.

In one embodiment, the softenable material of the fourth layer 80 comprises a mixture of polycaprolactone. A suitable polycaprolactone is Tone™ Polymer P-767 from Union Carbide Corporation, 39 Old Ridgebury Road, Danbury, Conn. 06817-0001.

In a second embodiment, the softenable material of the fourth layer 100 comprises a mixture of polycaprolactone and ethylene vinyl acetate (EVA) such as ELVAX®.

In a third embodiment, the softenable material of the fourth layer 100 comprises ethylene vinyl acetate (EVA) alone, such as ELVAX®.

In a fourth embodiment, the softenable material of the fourth layer 100 comprises a mixture of polycaprolactone and a polyolefin elastomer. Preferably, the polyolefin elastomer is a copolymer of ethylene and octene-1. A suitable copolymer is available as ENGAGE® from Dupont Canada, Inc., P.O. Box 2200, Streetsville, Mississauga, Ontario L5M 2H3.

Figure 8:
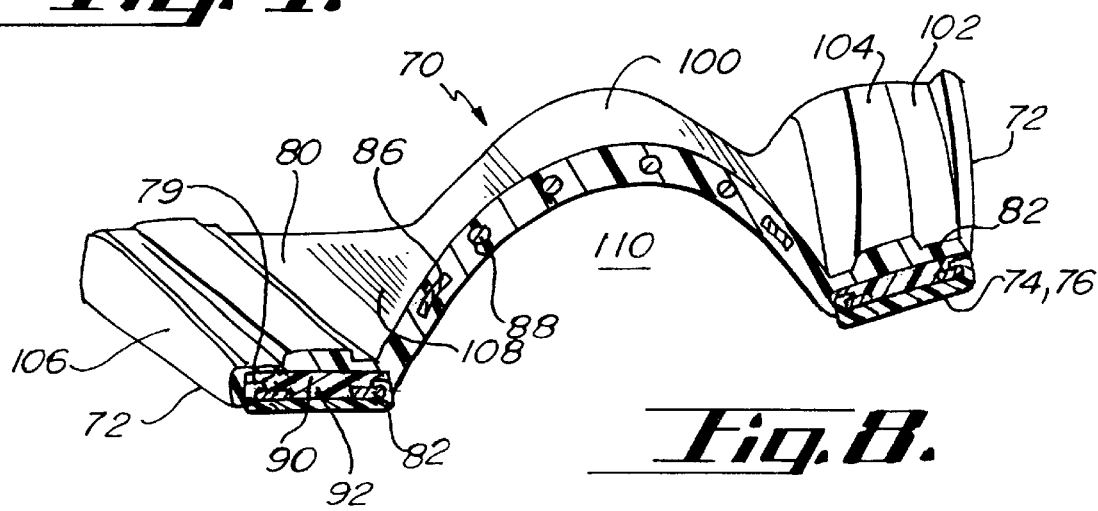
FIG. 8 is a cross-section of the dental appliance of the present invention taken at approximately the lines 8—8 of FIG. 4.

As can be seen best in FIG. 8, the softenable material of the fourth layer 100 extends downwardly over encapsulating the second and third layers, forming the labial wall 82 of the appliance and leaving only the tread 76 of traction pads 74 exposed.

The four layers are bonded together. In addition, the bite plate 90 and framework 80 are further interlocked with the first layer 74 by projections 77 in the first layer mating with apertures 94 in the bite plate.

Figure 2:
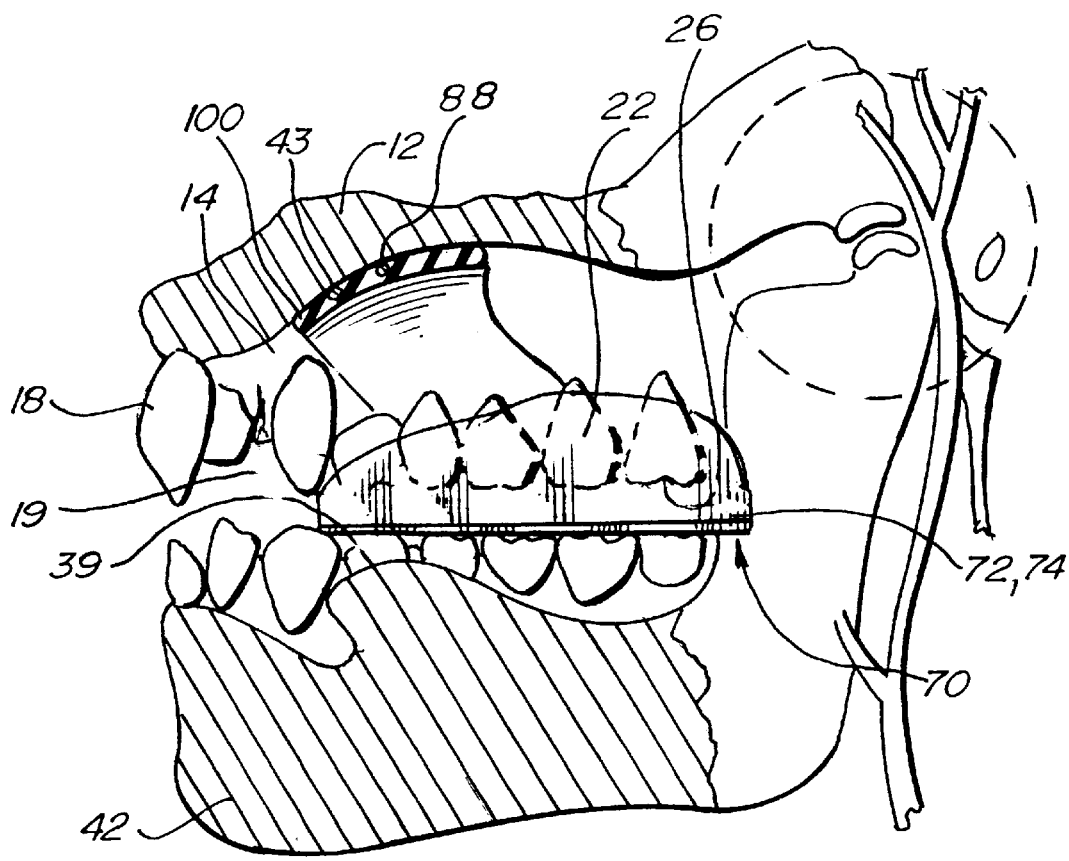
FIG. 2 is similar to FIG. 1, but shows the dental appliance of the present invention in place.
Figure 5:
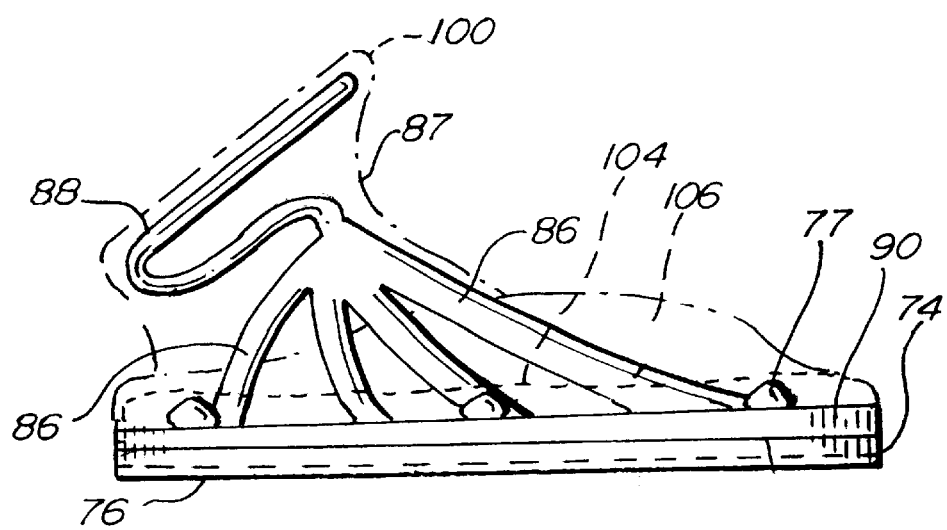
FIG. 5 is a side elevational view with the fourth arch material in phantom outline of the dental appliance of the present invention.
Figure 6:
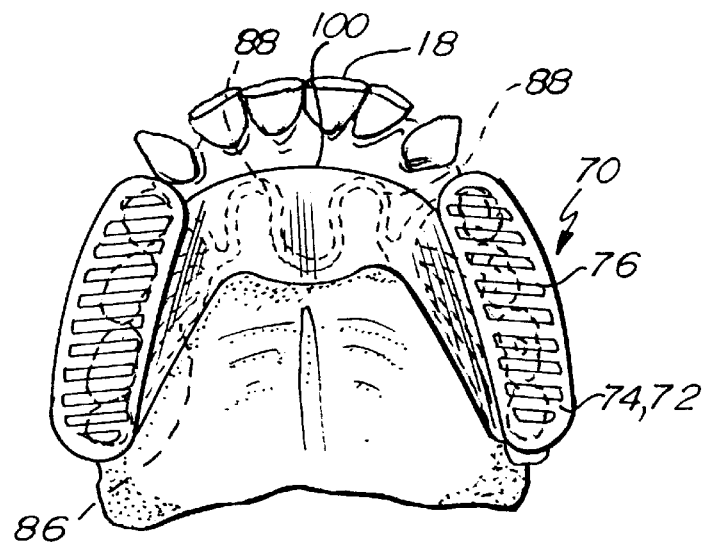
FIG. 6 is a bottom plan view of the dental appliance of the present invention in place in the mouth.
Figure 7:
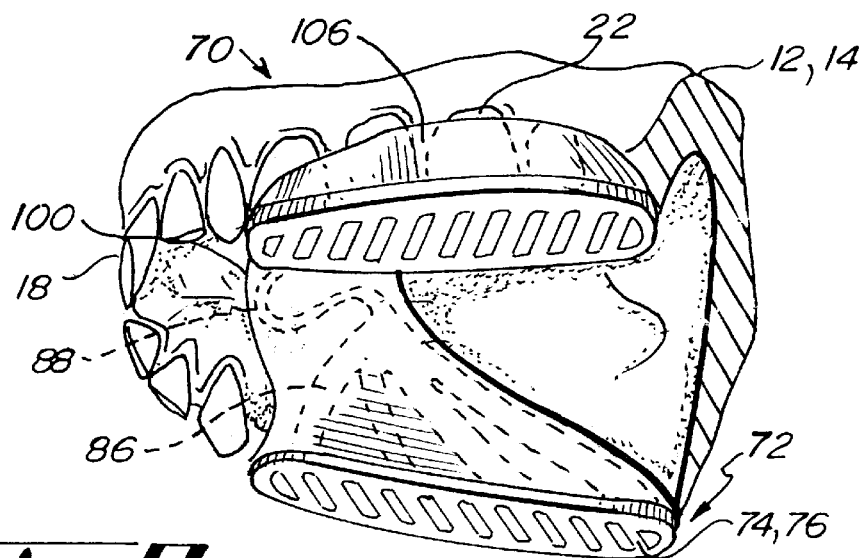
FIG. 7 is a bottom perspective view of the dental appliance of the present invention in place in the mouth.

The dental appliance 70 further comprises a continuous vertical arch 100 open anteriorly and posteriorly, extending from the fourth layer 100 of the occlusal pads 72 and constructed from the softenable material of the fourth layer 100. As best seen in FIGS. 2 and 5, the arch 100 is canted forwardly from the occlusal pads 72 toward the anterior teeth 18 of the upper jaw 12, so that the arch 100 contacts the upper jaw 12 adjacent the gum tissue 14 of the anterior teeth 18 at the ruggae or anterior palate 43. The arch 100 is adapted to expand and contract to be molded to the anterior palate 43 and adapted to lie along the anterior palate out of the way of the tongue and extending directly across to and connecting the pads 72 together within the mouth and out of the way of the tongue to maintain the positions of the occlusal pads within the mouth and to prevent loss of the pads such as by swallowing. The arch fourth material 100 forms tooth channel 102 with central raised portion 104, labial wall 106 and lingual wall 108.

A tunnel 110 (FIG. 8) extends beneath the arch 86 and is defined by the arch 100 and the lingual walls 108. The tunnel 110 is open anteriorly and posteriorly to allow unobstructed movement of the tongue 39 anteriorly and posteriorly.

The framework 80 of the dental appliance 70 further preferably comprises a serpentine Belevedere bridge 88 embedded within the softenable material of the arch 100. The bridge 88 is expandable and contractible, thereby following the arch 100 as it is molded to the palate. Also, the bridge 88 does not soften as much as the arch 100 during heating, and therefore prevents the arch 100 from collapsing during the fitting process described below. The bridge 88 is preferably comprised of the non-softening material of the second layer 80 and is continuous with the Cross-cantilever connectors 86 which is connected to the occlusal pad plates 82. Thus, the appliance does not go limp upon heating as its shape is supported by the bridge 88, connectors 86 and pad plate 82.

To create the dental appliance 70 of the present invention, the second layer framework 80 is formed, including the occlusal pad plate 82 with openings 84 therethrough. Cross-cantilevered connectors 86 connect along the length of the pad plate 82 and join up with the serpentine Belevedere bridge 88 to give the appliance 70 rigidity while yet permitting the appliance to expand and contract laterally and upwardly as will be appreciated (see arrows in FIG. 4). Next, the third layer bite plate or reverse wedge 90 is formed having bosses or raised portions 92 on their underside along with apertures 94 extending therethrough. Next, the bite plate 90 has its bosses indexed into the openings 84 of the framework pad plate 82. The first layer traction pads are next formed with their locking knobs 76 extending up through openings 84 and apertures 94 locking the first 74, second 80, and third 90 layers together. Lastly, the fourth layer arch 100 is formed around the entire dental appliance 70, excepting the tread portion 76 of the traction pad 74. Tooth channel 102 was formed along with central raised portion 104, labial or buckle wall 106 and lingual or inner wall 108. Tunnel 110 is thus formed thereunder.

To prevent the traction pads 74 from shearing away from the bite plate 90, the projection 77 further comprises a curved portion 78 and thereby capturing and interlocking pads 74, framework 80 and bite plate 90. Preferably, the curved portion 78 is convex relative to the central axis X1, as shown in the Figures. This construction deters shearing.

Figure 9:
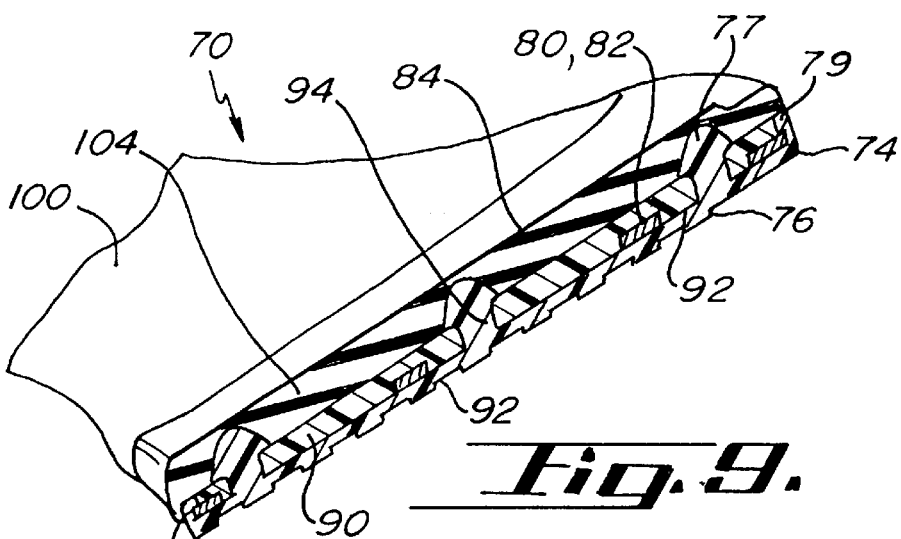
FIG. 9 is a cross-sectional view taken along lines 9—9 of FIG. 4 partially broken away at the arch.
Figure 10:
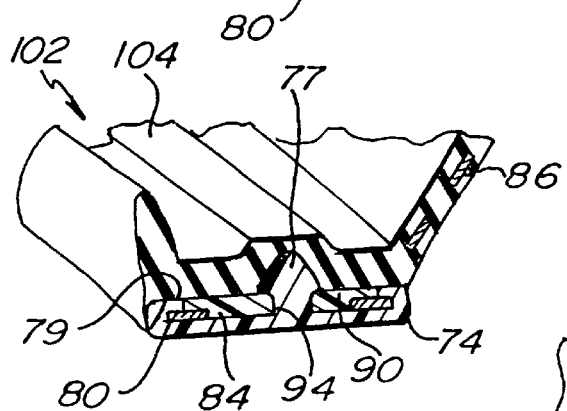
FIG. 10 is a cross-sectional view taken along lines 10—10 of FIG. 4 partially broken away showing the interlocking projections.
Figure 11:
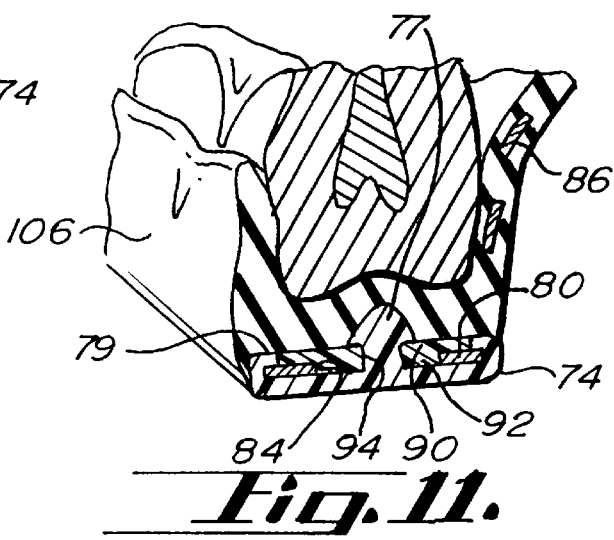
FIG. 11 is a view similar to FIG. 10 with the posterior teeth fitted to the appliance.
Figure 9A:
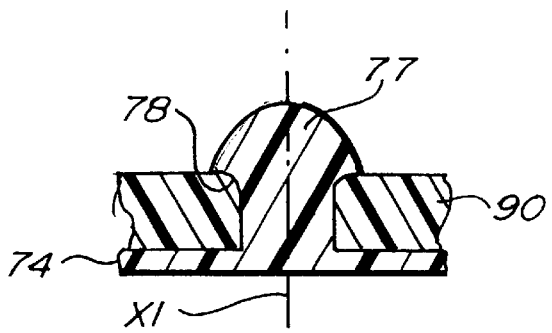
FIG. 9a is an enlarged, detailed and broken away view of the interlocking projections 77.

To further lock the traction pad 74 to the framework 80, a lip or retaining lid 79 integral with the traction pad 74 wraps over the pad plate 82 of the framework 80 like the lid of a bucket and thereby holds the appliance together as shown in FIGS. 9–11.

To fit the dental appliance 70 to the user's mouth, the dental appliance 70 is placed in hot water at about 212° Fahrenheit (i.e., water that has been brought to a boil and then taken off the heat) for about 15 seconds. The dental appliance is then removed from the hot water, and it will be very soft, but the framework 80 will hold the appliance's general shape. Excess water is allowed to drain off the appliance 70 by holding it with a spoon so that the walls 108 of the appliance 70 do not touch (they will stick to each other if brought together and will be very difficult to separate).

Next, the wearer carefully places the appliance 70 in the mouth so that the anterior portion of the appliance 70 touches or covers the eye teeth (the third set of teeth from the front) and extends backwards toward the molars, bites down firmly on the appliance 70 and pushes the tongue against the roof of the mouth. The Cross-cantilevered connectors guide the upper molars 22 into position on pads 72. With a strong sucking motion, the wearer draws out all air and water from the appliance 70. The projections or knobs 77 will index to the cusps of the molars 22.

With a thumb, the wearer presses the appliance 70 tight against the roof of the mouth and then uses his hands and fingers to press the outside of the cheeks against the appliance 70, as the fourth layer of raised portion 104 oozes inwardly and outwardly to form the lingual and buccal walls 108 and 106 respectively. Because there is no rigid lingual wall, the appliance 70 will fit any width of molar 22 or mouth.

The wearer retains the appliance 70 in the mouth for at least one minute and, with the appliance 70 still in the mouth, takes a drink of cold water. Next, the wearer removes the appliance 70 from the mouth and places it in cold water for about 30 seconds.

The present invention may be embodied in other specific forms without departing from the spirit or essential attributes thereof; therefore, the illustrated embodiment should be considered in all respects as illustrative and not restrictive, reference being made to the appended claims rather than to the foregoing description to indicate the scope of the invention.

We claim:

1. A performance enhancing and force absorbing quadruple composite dental appliance, comprising:
   (a) a pair of traction pads of durable resilient material;
   (b) a framework connecting the pads of non-softenable, flexible, expandable, contractible material;
   (c) wedge-shaped bite plate of hard, very durable material on top of the pads; and
   (d) a softenable, impressionable material enclosing the bite plate, the framework and partially the traction pads.

2. The appliance of claim 1, wherein the materials are mechanically interlocked.

3. The appliance of claim 1, wherein the framework further comprises pad plates adjacent the traction pads, Cross-cantilevered connectors extending inwardly from the pads forming into the serpentine bridge.

4. The appliance of claim 1, wherein the wedge is thicker posteriorly and thinner anteriorly.

5. The appliance of claim 1, wherein the softenable, impressionable material forms a posterior tooth channel with a central raised portion and labial and lingual walls to accept teeth of any width.

6. The appliance of claim 1, wherein the softenable, impressionable material and embedded framework form an anteriorly canted arch which in the mouth extends across the anterior palate or ruggae.

7. The appliance of claim 1, wherein the softenable, impressionable material is formed from at least one of the following group comprising polycaprolactone, ethylene vinyl acetate and polyolefin elastomer.

8. The appliance of claim 1, wherein the traction pads have tread pattern to gap the cusps of the lower posterior teeth.

9. The appliance of claim 1, wherein the materials include an antimicrobial agent.

10. A performance enhancing and force absorbing quadruple composite dental appliance, comprising:
    (a) a pair of traction pads of durable resilient material;
    (b) a framework connecting the pads of non-softenable, flexible, expandable, contractible material comprising pad plates adjacent the traction pads Cross-cantilevered connectors extending inwardly from the pads forming into a serpentine bridge;
    (c) wedge-shaped bite plate of hard, very durable material on top of the pads; and
    (d) a softenable, impressionable material enclosing the bite plate, the framework and partially the traction pads form a tooth channel and labial wall.

11. The appliance of claim 10, wherein the materials are mechanically interlocked.

12. The appliance of claim 10, wherein the wedge is thicker posteriorly and thinner anteriorly.

13. The appliance of claim 10, wherein the softenable, impressionable material forms a posterior tooth channel with a central raised portion and labial and lingual walls.

14. The appliance of claim 10, wherein the softenable, impressionable material and embedded framework form an anteriorly canted arch which in the mouth extends across the anterior palate or ruggae.

15. The appliance of claim 10, wherein the softenable, impressionable material is formed from at least one of the following group comprising polycaprolactone, ethylene vinyl acetate and polyolefin elastomer.

16. The appliance of claim 10, wherein the traction pads have a tread pattern to gap the cusps of the lower posterior teeth.

17. The appliance of claim 10, wherein the materials include an antimicrobial agent.

18. A performance enhancing and force absorbing quadruple composite dental appliance, comprising:
    (a) a pair of traction pads of durable resilient material;
    (b) anteriorly canted arch connecting the pads of non-softenable, flexible, expandable, contractible material adapted to lie along the anterior palate or ruggae;
    (c) wedge-shaped bite plate of hard, very durable material on top of the pads; and
    (d) a softenable, impressionable material enclosing the bite plate, partially the traction pads and forming the arch.

19. The appliance of claim 18, wherein the materials are mechanically interlocked.

20. The appliance of claim 18, further comprising a framework which comprises pad plates adjacent the traction pads, Cross-cantilevered connectors extending inwardly from the pads forming into the serpentine bridge.

21. The appliance of claim 18, wherein the wedge is thicker posteriorly and thinner anteriorly.

22. The appliance of claim 18, wherein the softenable, impressionable material forms a posterior tooth channel with a central raised portion and labial and lingual walls.

23. The appliance of claim 18, wherein the softenable, impressionable material is formed from at least one of the following group comprising polycaprolactone, ethylene vinyl acetate and polyolefin elastomer.

24. The appliance of claim 18, wherein the traction pads have a tread pattern to gap the cusps of the lower posterior teeth.

25. The appliance of claim 18, wherein the materials include an antimicrobial agent.

26. A performance enhancing and force absorbing quadruple composite dental appliance, comprising:
   (a) a pair of traction pads of durable resilient material;
   (b) a framework connecting the pads in an anteriorly canted arch of nonsoftenable, flexible, expandable, contractible material;
   (c) a reverse wedge-shaped bite plate of hard, very durable material on top of the pads, wherein the pads, framework, and bite plate are mechanically interlocked; and
   (d) a softenable, impressionable material enclosing the bite plate, the framework and partially the traction pads.

27. The appliance of claim 26, wherein the materials are mechanically interlocked.

28. The appliance of claim 26, wherein the softenable, impressionable material is softenable by heat.

29. The appliance of claim 26, wherein the softenable, impressionable material comprises polycaprolactone.

30. The appliance of claim 26, wherein the softenable, impressionable material comprises ethylene vinyl acetate.

31. The appliance of claim 26, wherein the softenable, impressionable material comprises a mixture of polycaprolactone and ethylene vinyl acetate.

32. The appliance of claim 26, wherein the softenable, impressionable material comprises a mixture of polycaprolactone and a polyolefin elastomer.

33. The appliance of claim 32, wherein the polyolefin elastomer is a copolymer of ethylene and octene-1.

34. The appliance of claim 26, wherein the framework further comprises occlusal pad plates, a serpentine portion, and a cantilevered portion connecting the serpentine portion to the pad plates.

35. The appliance of claim 34, wherein the occlusal pad plates have openings therethrough, wherein the traction pads have upwardly directed knobs transiting the openings, and wherein the bite plate has apertures receiving and interlocking with the knobs to thereby lock the bite plate, pad plate, and traction pad together.

36. The appliance of claim 35, wherein the traction pad further comprises an integral retaining bucket lid that wraps over the pad plate of the framework to thereby hold the appliance together.

* * * * *